(12) United States Patent
Li et al.

(10) Patent No.: US 11,077,262 B2
(45) Date of Patent: Aug. 3, 2021

(54) MOUTHPIECE ASSEMBLY, ATOMIZER AND ELECTRONIC CIGARETTE HAVING SAME

(71) Applicant: Shenzhen First Union Technology Co., Ltd., Shenzhen (CN)

(72) Inventors: Yonghai Li, Shenzhen (CN); Zhongli Xu, Shenzhen (CN); Yikuan Zhu, Shenzhen (CN)

(73) Assignee: SHENZHEN FIRST UNION TECHNOLOGY CO., LTD., Shenzhen (CN)

( * ) Notice: Subject to any disclaimer, the term of this patent is extended or adjusted under 35 U.S.C. 154(b) by 579 days.

(21) Appl. No.: 15/614,604

(22) Filed: Jun. 5, 2017

(65) Prior Publication Data
US 2017/0265522 A1 Sep. 21, 2017

(30) Foreign Application Priority Data
Jun. 7, 2016 (CN) .......................... 201620543812.5

(51) Int. Cl.
*A61M 15/00* (2006.01)
*A24F 40/485* (2020.01)
(Continued)

(52) U.S. Cl.
CPC ........... *A61M 15/0021* (2014.02); *A24F 7/00* (2013.01); *A24F 40/485* (2020.01); *A24F 40/10* (2020.01); *A61M 11/042* (2014.02); *A61M 15/06* (2013.01)

(58) Field of Classification Search
CPC .... A24F 47/002; A24F 47/004; A24F 47/008; A24F 7/00; A24F 7/02; A24F 40/10;
(Continued)

(56) References Cited

U.S. PATENT DOCUMENTS

2014/0182609 A1 * 7/2014 Liu .................. A24F 47/008
131/329

FOREIGN PATENT DOCUMENTS

| CN | 105249535 | * | 1/2016 | ........... B67D 7/0288 |
| DE | 202014000343 | * | 2/2014 | ............... A24F 7/00 |
| EP | 3150507 A1 | * | 4/2017 | ........... B65D 47/265 |

OTHER PUBLICATIONS

DE202014000343 (Machine Translation) [online], [retrieved on Sep. 13, 2019], retrieved from ESPACENET(https://worldwide.espacenet.com/?locale=en_EP) (Year: 2014).*

(Continued)

*Primary Examiner* — Michael H. Wilson
*Assistant Examiner* — Yana B Krinker
(74) *Attorney, Agent, or Firm* — Cheng-Ju Chiang (57) ABSTRACT

The present disclosure relates to a mouthpiece assembly for an electronic cigarette. The mouthpiece assembly includes a mouthpiece, and a base defining an air inlet. The mouthpiece includes a sucking end, a connecting end, and an air passage. The sucking end defines an air outlet, and the air outlet is in communication with the air passage. The air inlet is in communication with the air passage. The mouthpiece assembly further includes a blocking element on the base. The blocking element is capable of preventing air from flowing through. The blocking element defines at least one through hole. The mouthpiece is capable of driving the blocking element to rotate relative to the base, so that an area of at least one opening formed by the at least one through hole and the air inlet can be changed.

8 Claims, 8 Drawing Sheets

(51) Int. Cl.
*A24F 7/00* (2006.01)
*A24F 40/10* (2020.01)
*A61M 11/04* (2006.01)
*A61M 15/06* (2006.01)

(58) Field of Classification Search
CPC ... A24F 40/485; A61M 11/042; A61M 15/06; A61M 15/0021
See application file for complete search history.

(56) References Cited

OTHER PUBLICATIONS

DE 202014000343 (Human Translation) [online], [retrieved on Sep. 2019], retrieved from LinguaLinx Language Solutions, Inc., Troy, NY (Year: 2014).*

* cited by examiner

MOUTHPIECE ASSEMBLY, ATOMIZER AND ELECTRONIC CIGARETTE HAVING SAME

TECHNICAL FIELD

The present invention relates to electronic cigarettes, and particularly to a mouthpiece, an atomizer and an electronic cigarette using same.

BACKGROUND ART

Nowadays, electronic cigarettes have been in widespread use. However, in a typical electronic cigarette, an amount of aerosol output cannot be adjusted, rendering user unsatisfactory.

What are needed, therefore, are a mouthpiece assembly, an atomizer and an electronic cigarette using same, which can overcome the above shortcomings.

SUMMARY

The present disclosure relates to a mouthpiece assembly for an electronic cigarette. The mouthpiece assembly includes a mouthpiece, and a base defining an air inlet. The mouthpiece includes a sucking end, a connecting end, and an air passage. The sucking end defines an air outlet, and the air outlet is in communication with the air passage. The air inlet is in communication with the air passage. The mouthpiece assembly further includes a blocking element on the base. The blocking element is capable of preventing air from flowing through. The blocking element defines at least one through hole. The mouthpiece is capable of driving the blocking element to rotate relative to the base, so that an area of at least one opening formed by the at least one through hole and the air inlet can be changed.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Several definitions that apply throughout this disclosure will now be presented.

The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

Figure 1:
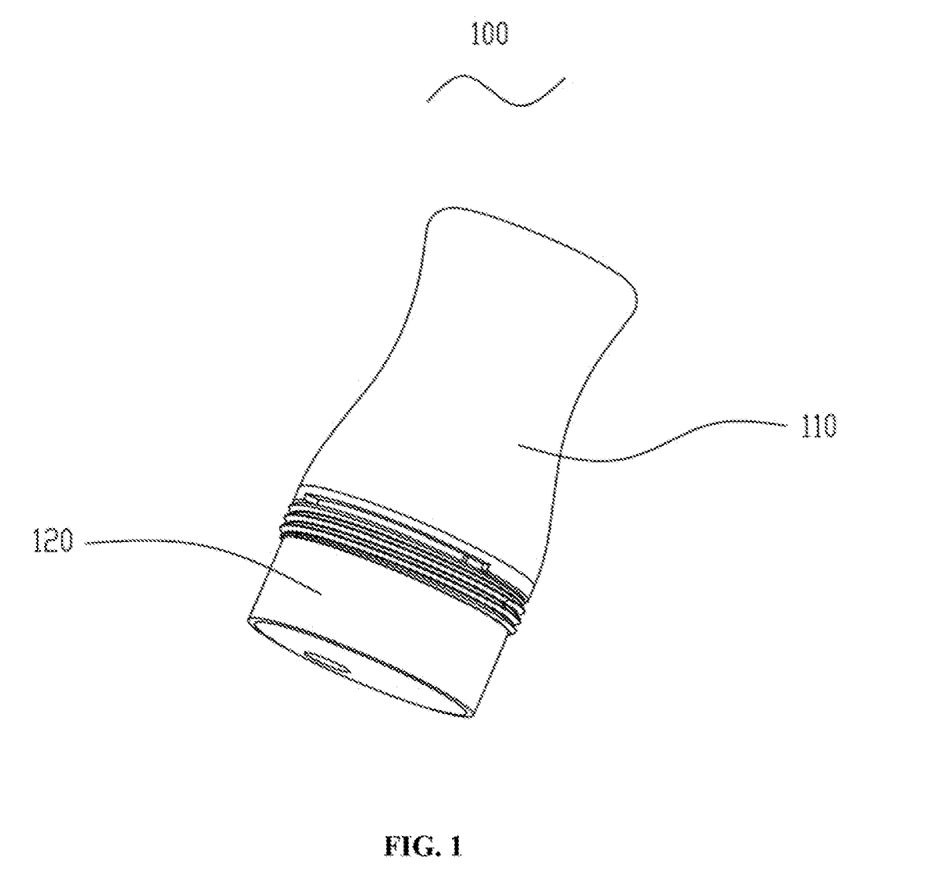
FIG. 1 is a perspective view of a mouthpiece assembly according to a first embodiment.
Figure 2:
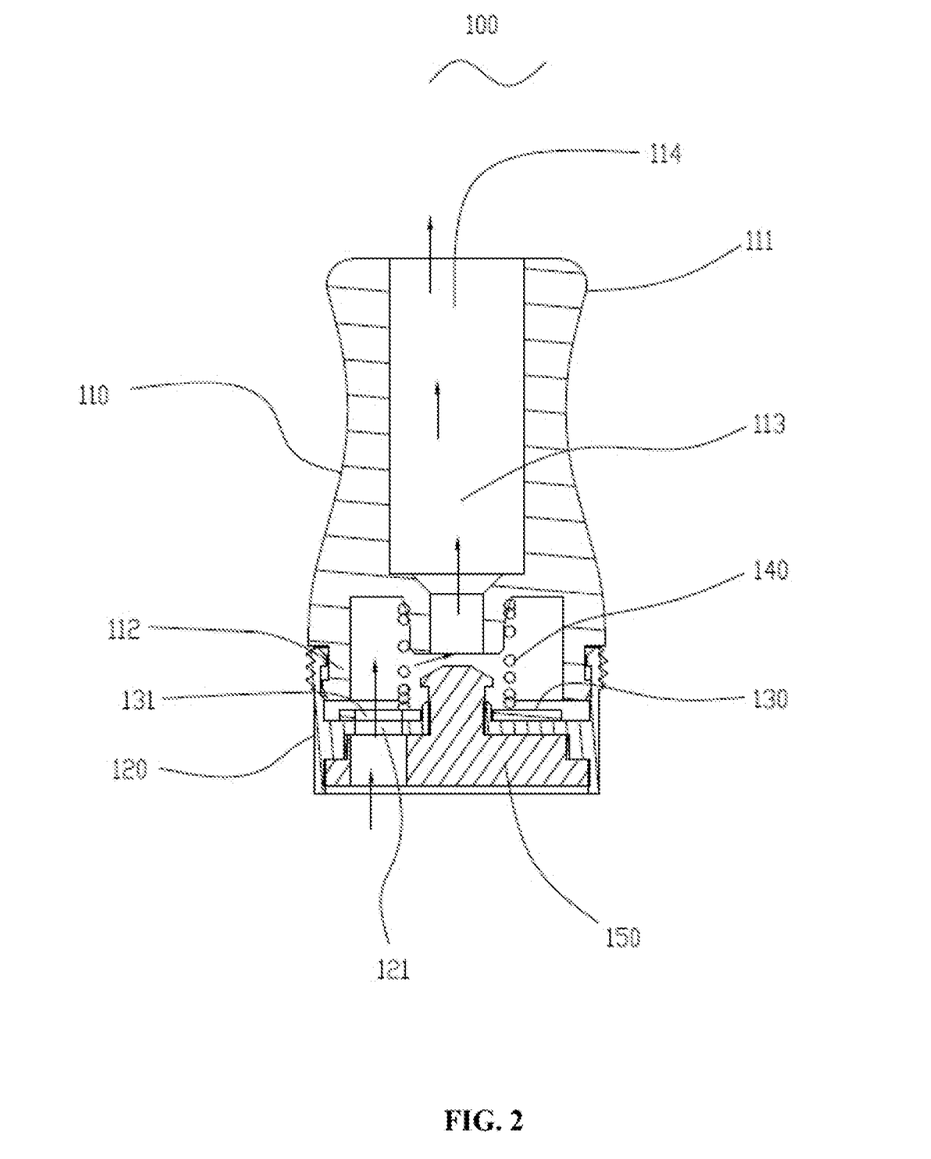
FIG. 2 is a cross-sectional view of the mouthpiece assembly of FIG. 1.

Referring to FIGS. 1-2, a mouthpiece assembly 100 is shown. The mouthpiece assembly 100 includes a mouthpiece 110 and a base 120. The mouthpiece 110 includes a sucking end 111, a connecting end 112 for connecting with the base 120, and an air passage 113 defined in the mouthpiece 110. The sucking end 111 defines an air outlet 114. The base 120 defines an air inlet 121. Both of the air inlet 121 and the air outlet 114 are in communication with the air passage 113. The base 120 further includes a blocking element 130 configured (i.e., structured and arranged) for blocking air from passing through. The blocking element 130 defines a through hole 131. The mouthpiece 110 is capable of driving the blocking element 130 to rotate relative to the base 120, so that an area of an opening formed by the through hole 131 and the air inlet 121 can be changed, thus adjusting an amount of air output from the air outlet 114. When the through hole 131 is miss-aligned with the air inlet 121, the blocking element 130 prevents air from passing through the air inlet 121. In the present embodiment, the blocking element 130 defines only one through hole 131, and the connecting end 112 and the base 120 are coupled by snap fit.

Figure 3:
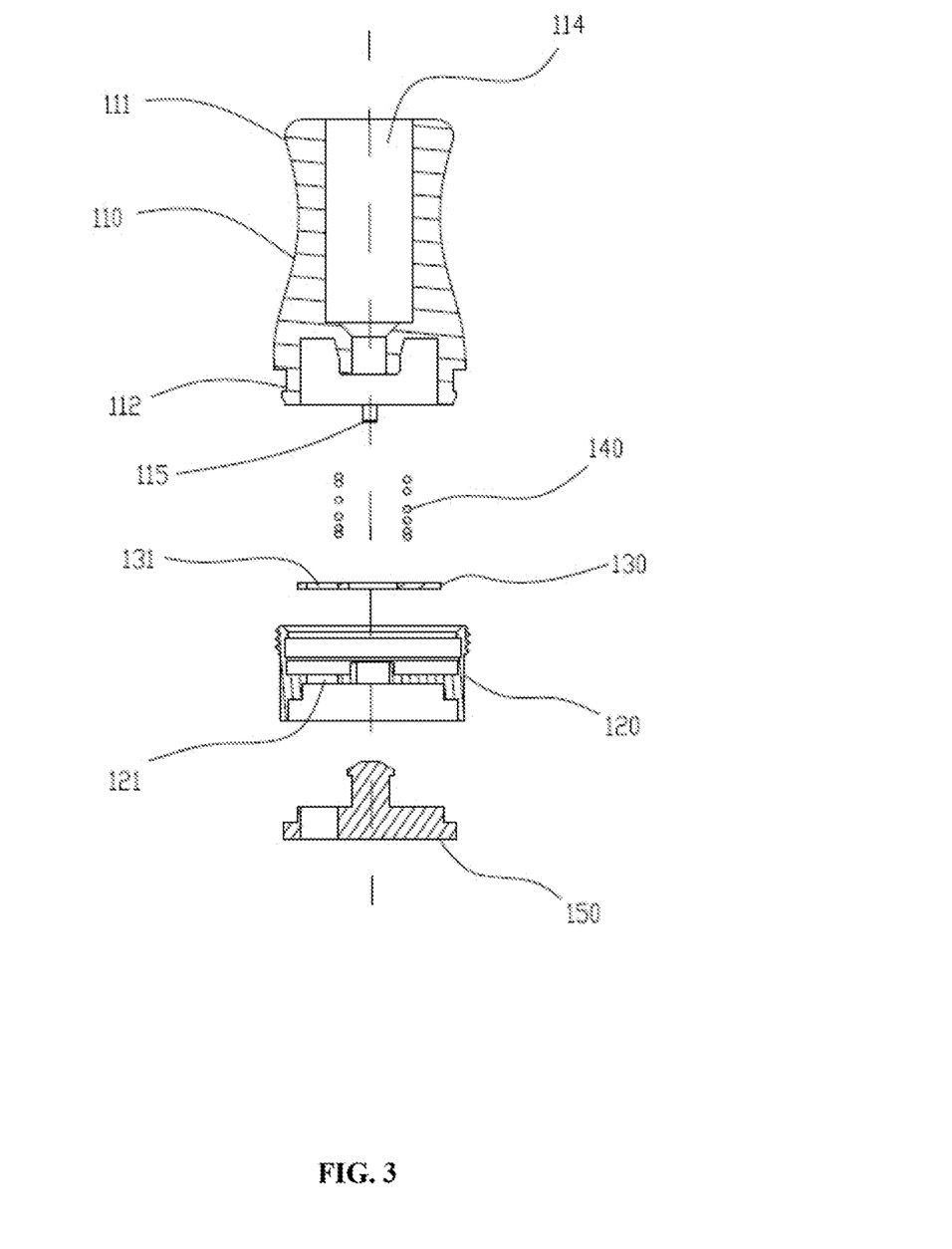
FIG. 3 is a cross-sectional exploded view of the mouthpiece assembly of FIG. 1.
Figure 4:
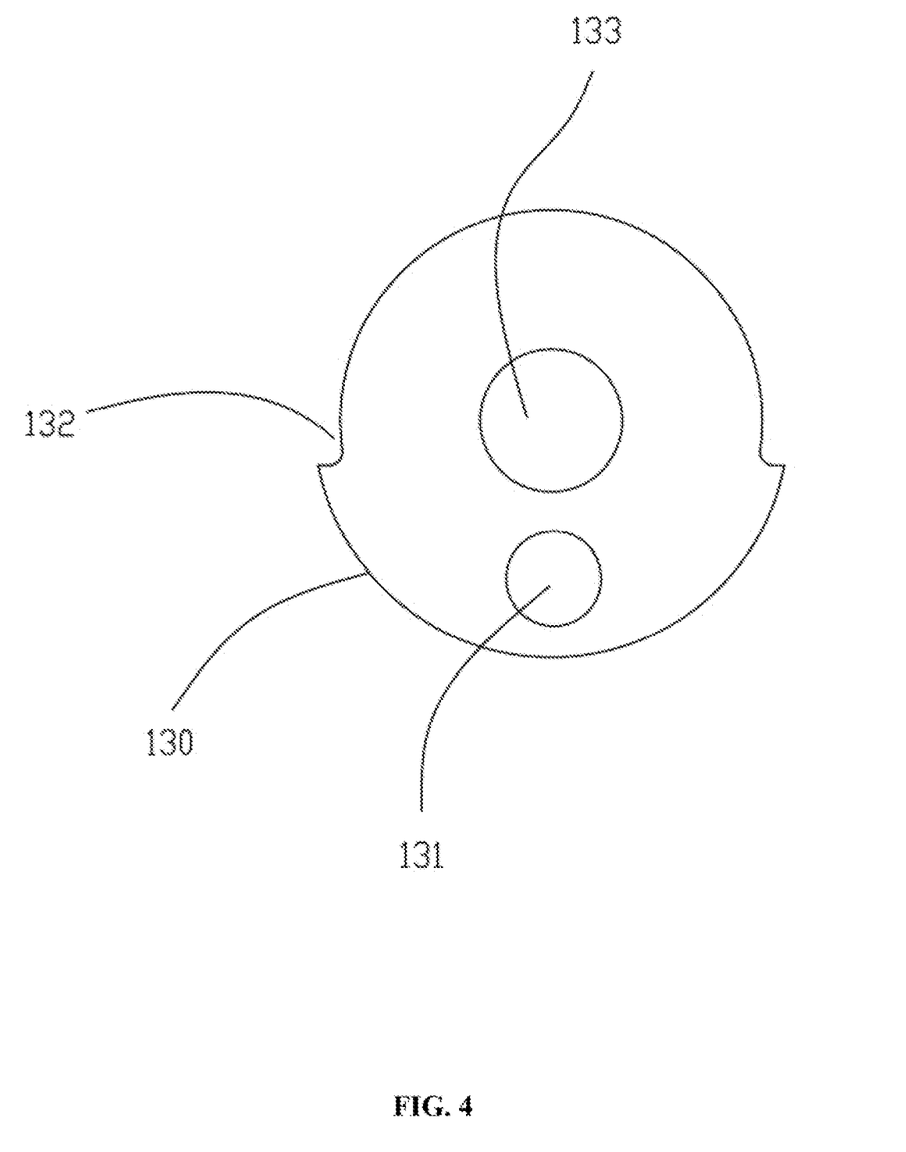
FIG. 4 is a top plan view of a blocking element of the mouthpiece assembly of FIG. 1.
Figure 5:
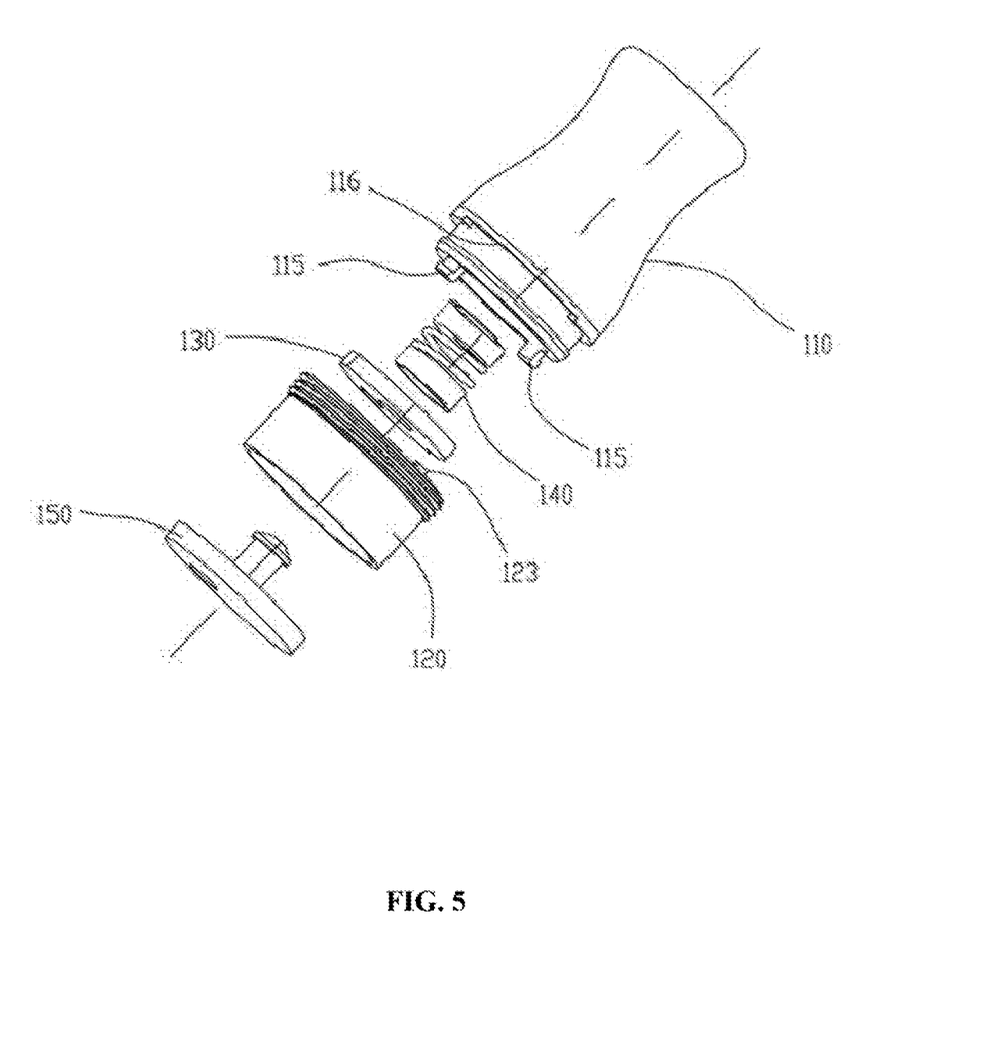
FIG. 5 is a perspective exploded view of the mouthpiece assembly of FIG. 1.
Figure 6:
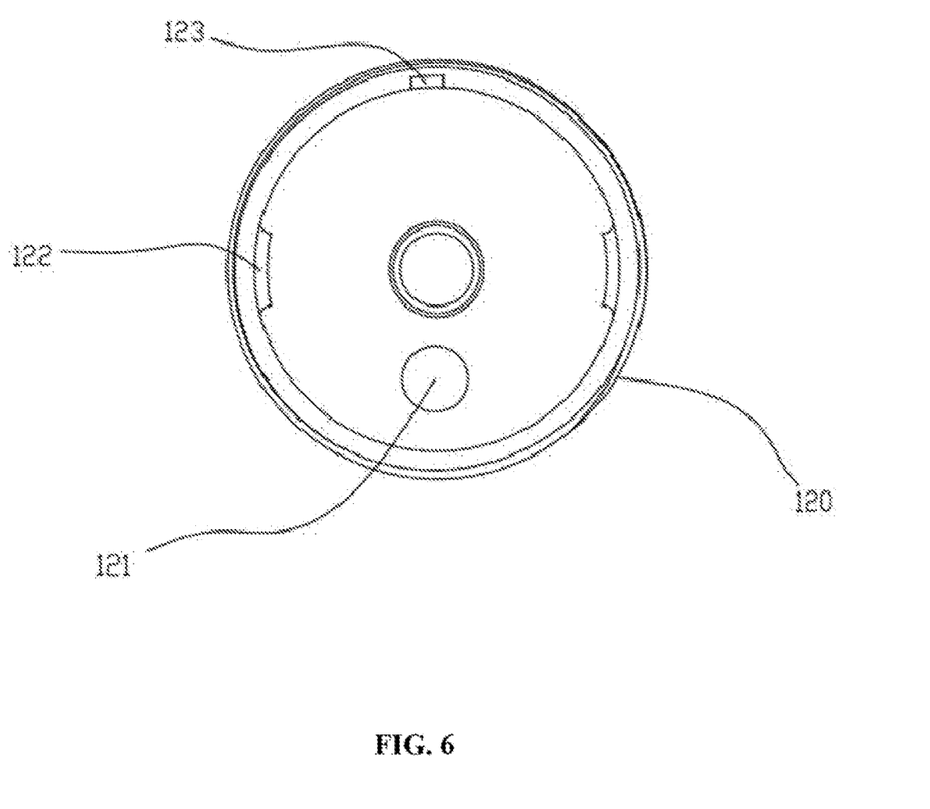
FIG. 6 is a top plan view of a base of the mouthpiece assembly of FIG. 1.

Referring to FIGS. 2-4, the mouthpiece 110 can expand and contract along an axial direction of the mouthpiece 110 relative to the base 120. The mouthpiece 110 further includes two protrusions 115 at the connecting end 112. The blocking element 130 defines a notch 132 and an assembling hole 133. The notch 132 matches with the protrusions 115. The blocking element 130 is assembled to the base 120 via the assembling hole 133. The mouthpiece 110 contracts along the axial direction relative to the base 120, until the protrusions 115 are engaged in the notch 132. In this position, the mouthpiece 110 is capable of driving the blocking element 130 to rotate. Referring to FIGS. 5 and 6, the protrusions 115 respectively are buckle structures, and the base 120 defines two recesses 122 matching with the protrusions 115. When the mouthpiece 110 is rotated, the mouthpiece 110 drives the blocking element 130 to rotate. When the through hole 131 is aligned with the air inlet 121, the protrusions 115 are engaged in the recesses 122, thus limiting an axial movement between the mouthpiece 110 and the base 120. In other embodiments, the protrusions 115 may be formed on the blocking element 130, and the notch 132 may be defined in the mouthpiece 110.

Referring to FIGS. 2 and 5, in the present embodiment, an elastic element 140 is provided between the blocking element 130 and the mouthpiece 110. The protrusions 115 are engaged in the notches 132 only after the mouthpiece 110 have conquered an elastic force of the elastic element 140. Referring to FIG. 5, a stop means is provided between the mouthpiece 110 and the base 120, and is configured for limiting a rotating angle of the mouthpiece 110 relative to the base 120. The stop means includes a protruding rod 123, and a sliding slot 116 matching with the protruding rod 123. The protruding rod 123 is formed on one of the mouthpiece 110 and the base 120, while the sliding slot 116 is defined in the other of the mouthpiece 110 and the base 120. In the present embodiment, the protruding rod 123 is formed on the base 120, and the sliding slot 116 is defined in the mouthpiece 110. The sliding slot 116 restricts an operating path of the protruding rod 123, thus limiting the rotating angle of the mouthpiece 110 relative to the base 120.

In other embodiments, referring to FIGS. 2, 3 and 5, a flexible element 150 may be arranged on the base 120. The flexible element 150 is configured for ensuring an air tightness of the mouthpiece assembly 100, when the base 120 is connected to an external structure.

Figure 7:
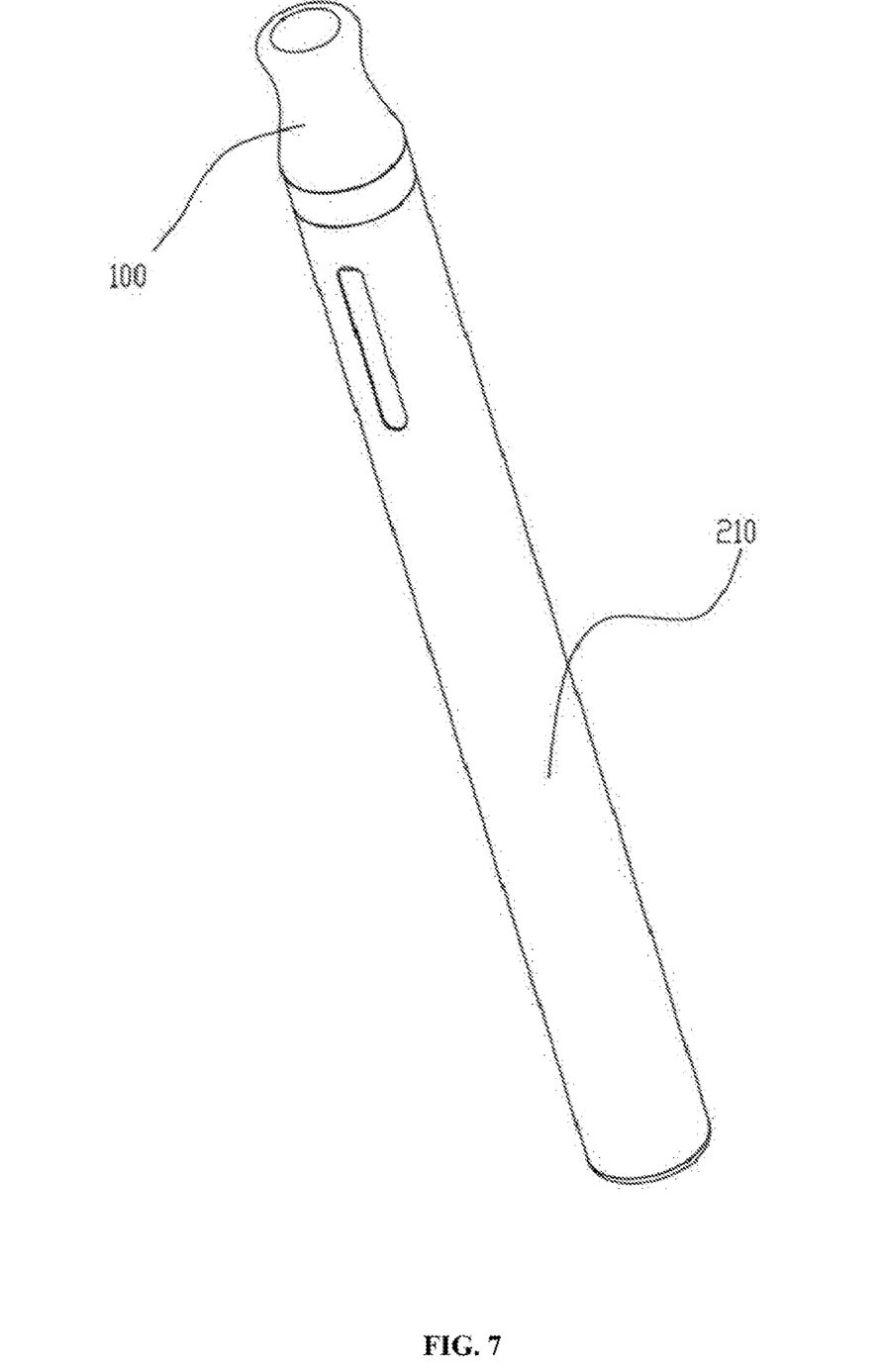
FIG. 7 is a perspective view of an electronic cigarette according to a second embodiment.
Figure 8:
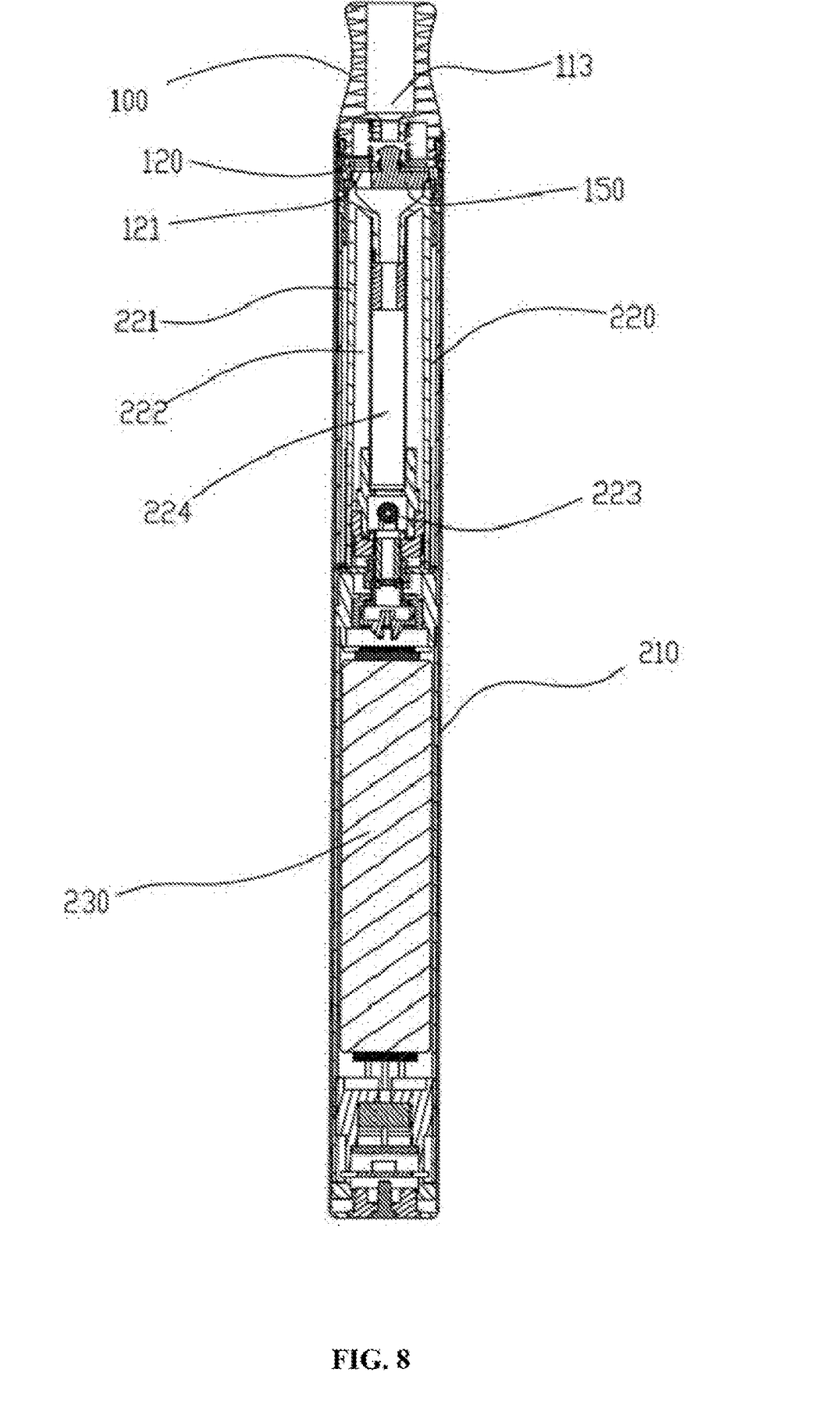
FIG. 8 is a cross-sectional view of the electronic cigarette of FIG. 7.

Referring to an electronic cigarette is shown. The electronic cigarette includes a housing 210, an atomizer 220 arranged in the housing 210, and a power supply 230. The power supply 230 is configured for feeding the atomizer 220 power. The atomizer 220 includes a shell 221, the mouthpiece assembly 100 connected at an end of the shell 221. A liquid chamber 222, an atomizing element 223, and an aerosol passage 224 are arranged in the shell 221. The liquid chamber 222 is configured for containing tobacco liquid. The atomizing element 223 is configured for atomizing the tobacco liquid to form aerosol. The aerosol passage 224 allows aerosol to pass through. The air passage 113 is in communication with the aerosol passage 224 via the air inlet 121.

Referring to FIGS. 7-8, a flexible element 150 is further provided on the base 120. The flexible element 150 is arranged at an end of the base 120 with the air inlet 121. The flexible element 150 keeps the air inlet 121 in communication with the aerosol passage 224. The flexible element 150 is configured for ensuring an airtight connection between the air inlet 121 and the aerosol passage 224, when the base 120 is connected to the shell 221. The flexible element 150 is made of silicone or rubber.

In the present embodiment, the atomizer 220 and the power supply 230 are arranged in the housing 210 to form a one-piece structure. It is to be understood that, in other embodiments, the power supply 230 may be detachably coupled with the atomizer 220.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. A mouthpiece assembly for an electronic cigarette, comprising:
   a mouthpiece, the mouthpiece is movable to expand and contract along an axial direction of the mouthpiece between a first position and a second position in reaction to an external force, the mouthpiece comprising a sucking end, a connecting end, and an air passage, the sucking end defining an air outlet, the air outlet being in communication with the air passage;
   a base defining an air inlet, the air inlet being in communication with the air passage;
   wherein, and the mouthpiece assembly comprises a blocking element on the base, the blocking element is capable of preventing air from flowing through, the blocking element defines at least one through hole, the mouthpiece assembly further comprises a protrusion and a notch, the protrusion is formed on one of the connecting end and the blocking element, the notch is defined in the other of the connecting end and the blocking element, an elastic element is provided between the blocking element and the mouthpiece, the mouthpiece is capable of driving the blocking element to rotate relative to the base along a rotating direction, which is not parallel to the axial direction, via engagement between the protrusion and the notch along the rotating direction when the mouthpiece is moved by the external force from the first position to the second position along the axial direction to engage the mouthpiece with the blocking element by conquering an elastic force of the elastic element, so that an area of at least one opening formed by the at least one through hole and the air inlet can be changed, and the mouthpiece is unable to drive the blocking element to rotate when the mouthpiece is located in the first position and disengages from the blocking element.

2. The mouthpiece assembly according to claim 1, wherein the protrusion has a buckle structure, the base defines a recess matching with the protrusion, when the at least one through hole is aligned with the air inlet, the protrusion is engaged in the recess, thus limiting an axial movement between the mouthpiece and the base.

3. The mouthpiece assembly according to claim 1, further comprising a stop means between the mouthpiece and the base, wherein the stop means is configured for limiting a rotating angle of the mouthpiece relative to the base, the stop means comprises a protruding rod and a sliding slot matching with the protruding rod, the protruding rod is formed on one of the mouthpiece and the base, and the sliding slot is defined in the other of the mouthpiece and the base.

4. The mouthpiece assembly according to claim 1, wherein the connecting end and the base are coupled by snap fit.

5. An atomizer for an electronic cigarette, comprising:
   a housing;
   a mouthpiece assembly, the mouthpiece assembly being arranged at an end of the housing, comprising:
      a mouthpiece, the mouthpiece is movable to expand and contract along an axial direction of the mouthpiece between a first position and a second position in reaction to an external force, the mouthpiece comprising a sucking end, a connecting end, and an air passage, the sucking end defining an air outlet, the air outlet being in communication with the air passage;

a base defining an air inlet, the air inlet being in communication with the air passage;

wherein the mouthpiece assembly further comprises a blocking element on the base, the blocking element is capable of preventing air from flowing through, the blocking element defines at least one through hole and a notch, the mouthpiece comprises a protrusion movable into the notch along the axial direction when the mouthpiece is moved from the first position to the second position and movable out of the notch along a reverse direction of the axial direction when the mouthpiece is moved from the second position to the first position, the mouthpiece is capable of driving the blocking element to rotate relative to the base along a rotating direction not parallel to the axial direction when the mouthpiece is moved by the external force from the first position to the second position along the axial direction to engage the mouthpiece with the blocking element via the protrusion engaging with a sidewall of the notch along the rotating direction, so that an area of at least one opening formed by the at least one through hole and the air inlet can be changed, and the mouthpiece is unable to drive the blocking element to rotate when the mouthpiece is located in the first position and disengages from the blocking element and the protrusion stays out of the notch;

a liquid chamber in the housing, the liquid chamber being configured for storing tobacco liquid;

an atomizing element in the housing, the atomizing element being configured for atomizing the tobacco liquid to form aerosol; and an aerosol passage allowing the aerosol to pass through;

wherein the base is connected to the end of the housing, and the air passage is in communication with the aerosol passage via the air inlet.

6. The atomizer according to claim 5, further comprising a flexible element on the base, wherein the flexible element is arranged at an end of the base with the air inlet, the flexible element keeps the air inlet in communication with the aerosol passage, the flexible element is configured for achieving an airtight connection between the air inlet and the aerosol passage.

7. An electronic cigarette, comprising:
an atomizer comprising:
a housing;
a mouthpiece assembly, the mouthpiece assembly being arranged at an end of the housing, comprising:

a mouthpiece, the mouthpiece is movable to expand and contract along an axial direction of the mouthpiece between a first position and a second position in reaction to an external force, the mouthpiece comprising a sucking end, a connecting end, and an air passage, the sucking end defining an air outlet, the air outlet being in communication with the air passage;

a base defining an air inlet, the air inlet being in communication with the air passage;

wherein, and the mouthpiece assembly comprises a blocking element on the base, the blocking element is capable of preventing air from flowing through, the blocking element defines at least one through hole, the mouthpiece assembly further comprises a protrusion and a notch, the protrusion is formed on one of the connecting end and the blocking element, the notch is defined in the other of the connecting end and the blocking element, the mouthpiece is capable of driving the blocking element to rotate relative to the base along a rotating direction non-parallel to the axial direction when the mouthpiece is moved by the external force from the first position to the second position along the axial direction to engage the mouthpiece with the blocking element via the protrusion engaging with the notch along the rotating direction, so that an area of at least one opening formed by the at least one through hole and the air inlet can be changed, and the mouthpiece is unable to drive the blocking element to rotate when the mouthpiece is located in the first position and disengages from the blocking element;

a liquid chamber in the housing, the liquid chamber being configured for storing tobacco liquid;

an atomizing element in the housing, the atomizing element being configured for atomizing the tobacco liquid to form aerosol; and an aerosol passage allowing the aerosol to pass through;

wherein the base is connected to the end of the housing, and the air passage is in communication with the aerosol passage via the air inlet; and a power supply configured for supplying the atomizer power.

8. The electronic cigarette according to claim 7, wherein the atomizer is detachably connected with the power supply.

* * * * *